US008354007B2

(12) United States Patent
Sukopp et al.

(10) Patent No.: US 8,354,007 B2
(45) Date of Patent: Jan. 15, 2013

(54) METHOD FOR PRODUCING AND PURIFYING TRIFLUOROMETHANESULFINIC ACID

(75) Inventors: Martin Sukopp, Mannheim (DE); Alexander Korte, Neustadt (DE); Stefan Fülster, Worms (DE); Michael Keil, Freinsheim (DE); Michael Rack, Eppelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/121,973

(22) PCT Filed: Sep. 28, 2009

(86) PCT No.: PCT/EP2009/062484
§ 371 (c)(1),
(2), (4) Date: Mar. 31, 2011

(87) PCT Pub. No.: WO2010/037693
PCT Pub. Date: Apr. 8, 2010

(65) Prior Publication Data
US 2011/0190510 A1 Aug. 4, 2011

(30) Foreign Application Priority Data
Oct. 2, 2008 (EP) .................................... 08165699

(51) Int. Cl.
*B01D 3/36* (2006.01)
*C07D 231/10* (2006.01)
*C07C 313/02* (2006.01)
(52) U.S. Cl. .................. 203/69; 548/367.4; 562/125
(58) Field of Classification Search ................. 203/69; 548/367.4; 562/125
See application file for complete search history.

(56) References Cited

U.S. PATENT DOCUMENTS

| 4,724,095 | A  | 2/1988 | Gresser      |
|-----------|----|--------|--------------|
| 5,618,945 | A  | 4/1997 | Casado et al.|
| 6,203,670 | B1 | 3/2001 | Forat et al. |
| 6,399,815 | B2 | 6/2002 | Suzuki       |

FOREIGN PATENT DOCUMENTS

| CN | 1 374 298      | 10/2002 |
|----|----------------|---------|
| DE | 198 53 560     | 5/2000  |
| EP | 0 165 136      | 12/1985 |
| EP | 0 295 117      | 12/1988 |
| EP | 0 668 269      | 8/1995  |
| EP | 1 331 222      | 7/2003  |
| WO | WO 99/32439    | 7/1999  |
| WO | WO 01/30760    | 5/2001  |
| WO | WO 2008/055877 | 5/2008  |
| WO | WO 2008/055879 | 5/2008  |
| WO | WO 2008/055880 | 5/2008  |
| WO | WO 2009/068533 | 6/2009  |

OTHER PUBLICATIONS

International Search Report prepared in International Application No. PCT/EP2009/062484, filed Sep. 28, 2009.
International Preliminary Report on Patentability from corresponding International Application No. PCT/EP2009/062484, filed Sep. 28, 2009.
Andrieux, C.P. et al., "Outer-Sphere and Inner-Sphere Processes in Organic Chemistry. Reaction of Trifluoromethyl Bromide with Electrochemically Generated Aromatic Anion Radicals and Sulfer Dioxide Anion Radicals", J. Am. Chem. Soc. 112, (1990), pp. 786-791.
Harzdorf, C. et al., "On Perfluoroalkanesulfinic acids", Liebigs Ann. Chem., 1973, pp. 33-39, Search Report Translation Provided.
Billard, Thierry, et al., "A New Equivalent of the CF3S(O)+ Cation. Synthesis of Trifluoromethanesulfinates andTrifluoromethanesulfinamides", Tetrahedron, 1999, p. 7243-7250, vol. 55.
Huilong, Yang et al., "Study on the Synthesis of Regent", Journal of Hebei University of Science and Technology, 2004, p. 69-73, vol. 25, No. 2, Translation provided.
Ren, Qing-Yun, et al., "Research Progress on Synthesis of Fipronil and its Main Intermediate", Chinese Journal of Pesticides, 2004, pp. 529-531, vol. 43, No. 12.
Roesky, H.W. et al., "Perfluoroalkansulfinsaeure-ester, -amide und isocyanate", Chem.Ber. 1974, p. 508-517, vol. 107, English translation provided.
Wakselman, Claude, et al., "Aryltrifluoromethylsulfoxides: Sulfinylation of Aromatics by Triflinate Salts in Acid Medium", Synlett, 2001, p. 550-552, No. 4.

*Primary Examiner* — Rebecca Anderson
*Assistant Examiner* — Samantha Shterengarts
(74) *Attorney, Agent, or Firm* — Brinks Hofer Gilson & Lione

(57) ABSTRACT

The invention relates to a process for purifying trifluoromethanesulfinic acid by azeotropic distillation with an aromatic solvent, to processes for preparing purified trifluoromethanesulfinic acid and to the use of the purified trifluoronnethanesulfinic acid for preparing trifluoromethylsulfinylated pyrazole derivatives, especially fipronil.

10 Claims, No Drawings

METHOD FOR PRODUCING AND PURIFYING TRIFLUOROMETHANESULFINIC ACID

This application is a National Stage application of International Application No. PCT/EP2009/062484, filed Sep. 28, 2009, the entire contents of which is hereby incorporated herein by reference. This application also claims priority under 35 U.S.C. §119 to European Patent Application No. 08165699.3, filed Oct. 2, 2008, the entire contents of which is hereby incorporated herein by reference.

The invention relates to a process for purifying trifluoromethanesulfinic acid, to processes for preparing purified trifluoromethanesulfinic acid and to the use of the purified trifluoromethanesulfinic acid for preparing trifluoromethylsulfinylated pyrazole derivatives, especially fipronil.

Trifluoromethanesulfinic acid ($CF_3$—$SO_2H$(I), TFMS hereinafter) and salts thereof find use as intermediates in organic synthesis, for example in the preparation of the insecticide fipronil (see, for example, U.S. Pat. No. 5,618,945, WO 2008/055 880, WO 2008/055 879 and WO 2008/055 877).

The literature already discloses various processes for preparing TFMS and salts thereof. According to EP-A 165,136, particular metals are reacted with a trifluoromethyl halide in the presence of sulfur dioxide in a polar aprotic solvent at a pressure of at least $10^8$ Pa. U.S. Pat. No. 6,203,670 describes the reaction of potassium trifluoroacetate with $SO_2$ in a polar aprotic solvent under the action of ultrasound. C. P. Andrieux et al. (J. Am. Chem. Soc. 112 (1990) 786-791) describe the reductive electrochemical reaction of $CF_3Br$ with $SO_2$. U.S. Pat. No. 6,399,815 describes the preparation of sulfinates by reducing sulfonyl chlorides with sulfites or hydrogensulfites in the presence of a hydrogenphosphate. WO 99/32439 describes the synthesis of fluorinated sulfinates by reacting fluorinated sulfonyl fluorides with $Na_2SO_3/NaHCO_3$ in an aqueous medium in the presence of a fluorinated surfactant or of an organic cosolvent having a boiling point below 110° C. C. Harzdorf et al. (Liebigs Ann. Chem. 1973, 33-39) describe the preparation of TFMS by reacting trifluoromethanesulfonyl fluoride with hydrazine in methanol, acidifying with HCl and subsequently fractionally distilling.

In spite of the methods specified, there is still a need for improvements, especially concerning the preparation of the free acid in pure form. It is therefore an object of the invention to provide an improved process for preparing TFMS in high purity.

It has been found that TFMS can be obtained in high purity by azeotropically distilling the crude product with a suitable organic solvent.

The invention therefore provides a process for purifying trifluoromethanesulfinic acid (TFMS) by initially charging TFMS as a crude product in an aromatic solvent which has a boiling point of <170° C., and performing an azeotropic distillation under a reduced pressure of from 0.1 to 500 mbar.

The invention further provides a process for preparing TFMS by
a) reacting a salt of TFMS with a nonvolatile acid which has a p$K_s$ of <−2, and
b) subjecting the resulting crude TFMS in a mixture with an aromatic solvent which has a boiling point of <170° C. to an azeotropic distillation at a reduced pressure in the range from 0.1 to 500 mbar.

The invention further provides a process for preparing fipronil by reacting the TFMS obtained by one of the above processes with a pyrazole derivative of the formula (I)

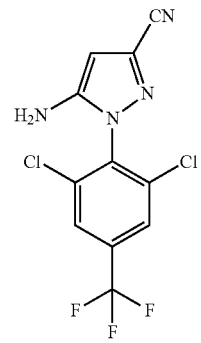

The process according to the invention affords TFMS in good yield and high purity, since the principal by-product of the reaction, the higher-boiling trifluoromethanesulfonic acid, does not form an azeotrope and can be removed easily with the bottoms of the distillation. A further by-product, the volatile trifluoroacetic acid, can likewise be removed by distillation as a first fraction. The dilution of the reaction mixture using solvent improves stirrability and heat transfer; the boiling point depression by the azeotrope enables a gentle distillation.

According to the invention, a mixture of TFMS crude product and an aromatic solvent with a boiling point of <170° C. is azeotropically distilled under a reduced pressure in the range from 0.1 to 500 mbar.

All boiling points are based, unless stated otherwise, on standard pressure (1 bar).

According to the invention, "azeotropic distillation" means that TFMS and aromatic solvent form an azeotropic mixture, i.e. a mixture in which, with advancing distillation, a point is reached at which the compositions of liquid phase(s) and gas phase become the same, which means that no further distillative separation is possible. TFMS and the aromatic solvent typically form a heteroazeotrope, i.e. the liquid phase is unstable in the azeotropic composition and separates into two phases. In the context of the invention, this can be utilized for simple removal of TFMS with a liquid-liquid phase separator.

Suitable aromatic solvents are all inert aromatic solvents having a boiling point of <170° C., preferably <150° C., more preferably <140° C., which form an azeotrope, preferably an azeotrope with a boiling point minimum. In the context of the invention, "inert" means that, under the conditions of the distillation, no reaction, or a reaction which lowers the yield to an extent which is not disadvantageous (below 5%, preferably below 1%), between TFMS and the aromatic solvent takes place.

Suitable aromatic solvents are listed by way of example in table 1.

TABLE 1

| Aromatic solvents | |
|---|---|
| Solvent | Boiling point ° C. |
| Benzene | 80 |
| Toluene | 110 |
| Xylene (o, m, p mixture) | 140 |
| Chlorobenzene | 132 |
| Bromobenzene | 156 |
| Fluorobenzene | 85 |
| Ethylbenzene | 136 |
| Anisole | 154 |

TABLE 1-continued

Aromatic solvents

| Solvent | Boiling point ° C. |
|---|---|
| Trifluoromethylbenzene | 102 |
| Isopropylbenzene | 152 |
| Mesitylene | 165 |
| Chlorotoluene (o, p, m) | 159-162 |

In order to be able to perform a viable distillation under reduced pressure, the boiling point of the aromatic solvent should preferably not be below 80° C.

Preference is given to benzene, fluorobenzene, anisole, trifluoromethylbenzene, toluene, xylene, ethylbenzene, isopropylbenzene and chlorobenzene. Particular preference is given to benzene, toluene, xylene, fluorobenzene, trifluoromethylbenzene, ethylbenzene and chlorobenzene. Especially preferred are toluene, xylene, ethylbenzene and chlorobenzene. Of course, it is also possible to use mixtures or two or more of the solvents mentioned.

The (weight) ratio of aromatic solvent to TFMS may vary within wide limits and is preferably from 1:100 to 100:1, more preferably from 1:3 to 10:1, especially from 1:1 to 4:1.

The mixture of crude TFMS and aromatic solvent can be effected by mixing the crude TFMS with the solvent. Preference is also given to taking up a salt of TFMS in the solvent and releasing TFMS therefrom by adding a strong acid.

Suitable column types for the distillation are all known types, for example columns with random packing, tray columns, columns with structured packing and dividing wall columns. Preference is given to columns with random packing and tray columns. In a further preferred embodiment of the process, the distillation is effected in a thin-film evaporator, falling-film evaporator or short-path evaporator, one of the latter apparatuses with an attached column of any kind, for example a column with structured packing, or more preferably a reaction vessel with attached column.

The distillation, which may be fractional, is effected, according to the solvent selected, generally within a temperature region (bottom) of less than 110° C., since there is otherwise the risk of decomposition of the TFMS. The distillation is performed under reduced pressure, preferably within a range from 0.1 to 500 mbar, preferably from 1 to 300 mbar, more preferably from 10 to 100 mbar, and the boiling point of the azeotrope should be taken into account.

The TFMS for purification in accordance with the invention may be prepared by any known processes, for example by one of the abovementioned processes.

Owing to the low stability of trifluoromethanesulfinic acid, this compound is generally handled and stored in the form of a salt. The invention therefore further provides a process for preparing TFMS, wherein TFMS is released by means of a strong acid from one of its salts and then purified by azeotropic distillation in accordance with the invention.

In principle, it is possible to use any desired salts of TFMS, preference being given to alkali metals, alkaline earth metals and ammonium salts, particular preference to alkali metal salts, especially the sodium and potassium salts.

It is of course also possible to use mixtures of two or more different salts.

Suitable acids for releasing the TFMS from the salt are nonvolatile acids having a $pK_s$ of <−2. In the context of the invention, "nonvolatile" means that the acid is nonvolatile under the conditions of the azeotropic distillation and preferably has a boiling point of at least 170° C. under standard pressure. Examples of suitable acids are strongly acidic ion exchangers, concentrated $H_3PO_4$ and $H_2SO_4$, especially in concentrated form (≧95% by weight of $H_2SO_4$), preference being given to $H_2SO_4$.

To release the TFMS, at least one equivalent of acid is needed; preferably from 1 to 10, more preferably from 1 to 2 and especially from 1 to 1.5 equivalents of acid are used.

The acid, especially concentrated sulfuric acid, can also be used as the solvent for the TFMS sulfinate. However, preference is given to suspending the salt in the aromatic solvent and then to adding the acids. Preference is further given to a continuous addition while cooling the reaction vessel.

The invention further provides a process for preparing the insecticide fipronil (II)

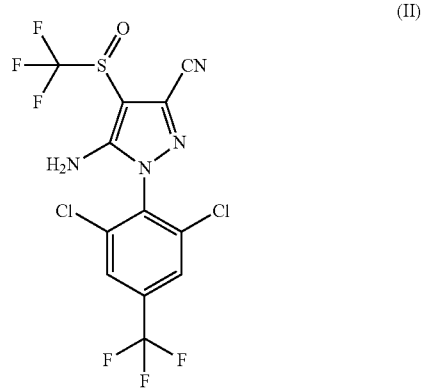 [SMILES: N#Cc1nn(-c2c(Cl)cc(C(F)(F)F)cc2Cl)c(N)c1S(=O)C(F)(F)F]

(II)

without further purification of the TFMS, for example by redistillation, by
a) reacting a salt of TFMS with a nonvolatile acid which has a $pK_s$ of <−2, and
b) azeotropically distilling the resulting crude TFMS in a mixture with an aromatic solvent which has a boiling point of <170° C. under reduced pressure and
c) reacting the resulting TFMS with a pyrazole derivative of the formula (I) (see above).

Various processes for reacting the pyrazole derivative (I) with TFMS to give fipronil (II) are described, for example, in U.S. Pat. No. 5,618,945, WO 2008/055 880, WO 2008/055 879 and WO 2008/055 877.

In a first variant (i) (WO 2008/055 880), the phenylpyrazole derivative (I) is reacted with TFMS with addition of a halogenating agent in the presence of an acid/amine complex, the amine being a secondary or tertiary amine and the acid used being HF, HCl, HBr, HI or a sulfonic acid derivative, and the reaction temperature not exceeding 39° C. at any time.

In a second variant (ii) (WO 2008/055 879), the phenylpyrazole derivative (I) is reacted with TFMS with addition of a halogenating agent in the presence of an acid/amine complex, the amine being a cyclic secondary amine and the acid used being a sulfonic acid derivative.

In a third variant (iii) (WO 2008/055 877), the phenylpyrazole derivative (I) is reacted with TFMS with addition of a halogenating agent in the presence of an acid/mine complex, the amine being a tertiary amine and the acid used being HF, HCl, HBr, HI or a sulfonic acid derivative.

In all three variants, the sulfinylation reaction proceeds as a two-stage process, wherein an addition of the $CF_3S(O)$ group onto the amino group of the pyrazole ring takes place in the first step, followed by a thia Fries rearrangement to give fipronil (II):

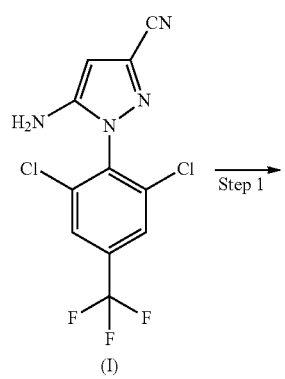

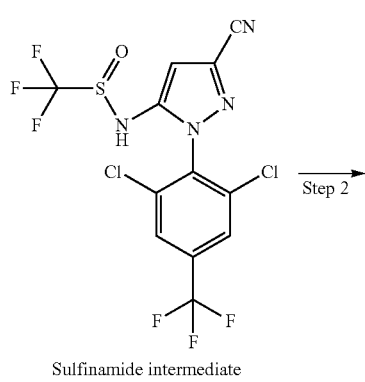

Sulfinamide intermediate

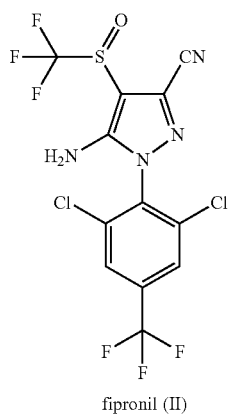

fipronil (II)

Details of the three variants can be found in the documents cited, which are hereby explicitly incorporated by reference, and whose content, where it relates to the reaction of TFMS, is considered to form part of this description by reference.

In a preferred embodiment of the process according to the invention, the TFMS distillate obtained in accordance with the invention is used directly without further purification for the reaction with the phenylpyrazole derivative (I).

TFMS obtained in accordance with the invention may, as well as the described use, find further use as an intermediate in organic synthesis, for example in the pharmaceutical industry, or for preparing photoinitiators for the free-radical polymerization of fluorinated monomers (see, for example, WO 99/32439).

The invention is illustrated in detail by the examples without restricting it thereby.

EXAMPLE 1

Azeotropic Distillation of Trifluoromethanesulfinic Acid with Ethylbenzene

In a 750 ml reactor with stirrer and distillation attachment, 92.7 g of potassium trifluoromethanesulfinate (0.50 mol, 92.5%) were suspended in 142 g of ethylbenzene. Subsequently, 75.0 g of concentrated sulfuric acid (0.75 mol, 98%) were added dropwise at from 20 to 30° C. with cooling within 15 min. The trifluoromethanesulfinic acid released thereby was azeotropically distilled off under a reduced pressure of 40 mbar at a condensate temperature of 46° C. within 5 h. The 69.4 g of lower phase of the distillate cooled to 5° C. consisted of trifluoromethanesulfinic acid and small amounts of ethylbenzene. The upper phase, which consisted predominantly of ethylbenzene, ran back into the reactor continuously during the distillation. The trifluoromethanesulfinic acid thus obtained (95% yield, 92% purity) can be used in subsequent reactions without further workup.

EXAMPLE 2

Azeotropic Distillation of Trifluoromethanesulfinic Acid with Chlorobenzene

In a 500 ml four-neck flask with stirrer and distillation attachment, 50.0 g of sodium trifluoromethanesulfinate (0.30 mol, 95.0%) were suspended in 144 g of monochlorobenzene (MCB). Subsequently, 48.5 g of concentrated sulfuric acid (0.48 mol, 97%) were added dropwise at from 20 to 30° C. with cooling within 10 min. The trifluoromethanesulfinic acid released thereby was azeotropically distilled off at a reduced pressure of 36 mbar and a condensate temperature of 37° C. within 6 h. The 40.1 g of lower phase of the distillate cooled to −20° C. consisted of trifluoromethanesulfinic acid and small amounts of MCB. The upper phase, which consisted principally of MCB, ran back into the reactor continuously during the distillation. The trifluoromethanesulfinic acid thus obtained (95% yield) can be used in subsequent reactions without further workup.

EXAMPLE 3

Azeotropic Distillation of Trifluoromethanesulfinic Acid with Toluene

In a 500 ml four-neck flask with stirrer and distillation attachment, 50.0 g of sodium trifluoromethanesulfinate (0.30 mol, 95.0%) were suspended in 112 g of toluene. Subsequently, 46.1 g of concentrated sulfuric acid (0.46 mol, 97%) were added dropwise at from 20 to 30° C. with cooling within 10 min. The trifluoromethanesulfinic acid released thereby was azeotropically distilled off at a reduced pressure of 50 to 150 mbar and a condensate temperature of from 31 to 51° C. within 9 h. The 34.2 g of lower phase of the distillate cooled to −20° C. consisted of trifluoromethanesulfinic acid and small amounts of toluene. The upper phase, which consisted principally of toluene, ran back into the reactor continuously during the distillation. The trifluoromethanesulfinic acid thus obtained (81% yield) can be used in subsequent reactions without further workup.

EXAMPLE 4

Azeotropic Distillation of Trifluoromethanesulfinic Acid with Ethylbenzene in the Presence of Trifluoromethanesulfonic Acid In a 750 ml reactor with stirrer and distillation attachment, 92.7 g of potassium trifluoromethanesulfinate (0.50 mol, 92.5%) were suspended in 142 g of ethylbenzene and 15.1 g of trifluoromethanesulfonic acid (0.1 mol, 99%). Subsequently, 75.0 g of concentrated sulfuric acid (0.75 mol, 98%) were added dropwise at from 20 to 30° C. with cooling within 15 min. The trifluoromethanesulfinic acid released thereby was azeotropically distilled off under a reduced pressure of 37 mbar at a condensate temperature of 46° C. within 5 h. The 57.8 g of lower phase of the distillate cooled to 5° C. consisted, according to 1H and 19F NMR, of trifluoromethanesulfinic acid, small amounts of ethylbenzene and traces of trifluoromethanesulfonic acid. The upper phase, which consisted predominantly of ethylbenzene, ran back into the reactor continuously during the distillation. The trifluoromethanesulfinic acid thus obtained (82% yield, 95% purity) can be used in subsequent reactions without further workup.

EXAMPLE 5

Azeotropic Distillation of Trifluoromethanesulfinic Acid with Ethylbenzene in the Presence of Trifluoroacetic Acid In a 1000 ml four-neck flask with stirrer and distillation attachment, a crude mixture of 50.8 g of potassium trifluoromethanesulfinate (0.29 mol, 98%) and 47.7 g of potassium trifluoroacetate (0.31 mol, 99%) was suspended in 258 g of ethylbenzene. Subsequently, 92.2 g of concentrated sulfuric acid (0.91 mol, 97%) were added dropwise at from 20 to 30° C. with cooling within 15 min. The trifluoroacetic acid released thereby was distilled off at a reduced pressure of 40 mbar within 20 min, while the trifluoromethanesulfinic acid which was likewise released was distilled off azeotropically at a reduced pressure of 40 mbar and a condensate temperature of from 42 to 46° C. within 3 h. The 30.0 g of lower phase of the distillate cooled to 5° C. consisted of trifluoromethanesulfinic acid and small amounts of ethylbenzene. The upper phase, which consisted principally of ethylbenzene, ran back into the reactor continuously during the distillation. The trifluoromethanesulfinic acid thus obtained (73% yield, 95% purity) can be used in subsequent reactions without further purification.

EXAMPLE 6

Use of Trifluoromethanesulfinic Acid Prepared in Accordance with the Invention for Synthesis of Fipronil A 500 ml jacketed reactor with stirrer, baffles and condenser was initially charged under a nitrogen atmosphere with 103 g of ethylbenzene, 6.3 g of dimethylisopropylamine hydrochloride (0.050 mol, 99%) and 15.5 g of potassium chloride (0.208 mmol). Subsequently, 31.5 g of trifluoromethanesulfinic acid (0.223 mol, 95.0%), 17.9 g of dimethylisopropylamine (0.203 mol, 99%) and 24.2 g of thionyl chloride (203 mmol, 99.7%) were metered in at 0° C. with cooling. After subsequently adding 54.8 g of 5-amino-3-cyano-1-(2,6-dichlor-4-trifluoromethylphenyl)pyrazole, the reaction mixture was stirred at 0° C. for 1 h, then heated to 35° C. over 45 min and stirred at 35° C. for a further 10 h. After the reaction had been quenched with sodium hydroxide solution and extracted with ethyl acetate and ethylbenzene, a nonisolated yield of fipronil of 80% was obtained in the crude solution (determination by means of quantitative HPLC).

The invention claimed is:
1. A process for purifying trifluoromethanesulfinic acid comprising azeotropically distilling a mixture comprising crude trifluoromethanesulfinic acid and an inert aromatic solvent having a boiling point of <170° C. under reduced pressure.
2. The process of claim 1, wherein the aromatic solvent is selected from the group consisting of benzene, fluorobenzene, anisole, trifluoromethylbenzene, toluene, xylene, ethylbenzene, isopropylbenzene and chlorobenzene.
3. The process of claim 1, wherein the weight ratio of aromatic solvent to trifluoromethanesulfinic acid is from 1:100 to 100:1.
4. The process of claim 1, wherein any trifluoroacetic acid present is removed in the first runnings.
5. The process of claim 1, further comprising removing any trifluoromethanesulfonic acid present from the bottoms of the distillation.
6. A process for preparing trifluoromethanesulfinic acid comprising:
   a) reacting a salt of trifluoromethanesulfinic acid with a nonvolatile acid which has a $pK_s$ of <−2; and
   b) azeotropically distilling the resulting crude trifluoromethanesulfinic acid in a mixture with an aromatic solvent which has a boiling point of <170° C. under reduced pressure.
7. The process of claim 6, wherein the nonvolatile acid is concentrated $H_2SO_4$.
8. A process for preparing fipronil comprising:
   a) reacting a salt of trifluoromethanesulfinic acid with a nonvolatile acid which has a $pK_s$ of <−2;
   b) azeotropically distilling the resulting crude trifluoromethanesulfinic acid in a mixture with an inert aromatic solvent which has a boiling point of <170° C. under reduced pressure; and
   c) reacting the resulting trifluoromethanesulfinic acid with a pyrazole derivative of the formula (I)

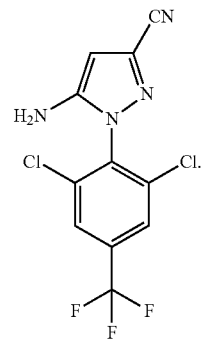

9. The process of claim 8, wherein the nonvolatile acid is $H_2SO_4$.
10. The process of claim 8, wherein the trifluoromethanesulfinic acid obtained in step b) is reacted directly without a further purification step.

* * * * *